United States Patent
Chen et al.

(10) Patent No.: US 11,311,546 B2
(45) Date of Patent: *Apr. 26, 2022

(54) METHOD FOR ENHANCING WOUND HEALING BY ADMINISTRATING ADENINE

(71) Applicant: Energenesis Biomedical Co., Ltd., Taipei (TW)

(72) Inventors: Han-Min Chen, Taipei (TW); Cheng-Yi Kuo, Taipei (TW); Chun-Fang Huang, Taipei (TW); Jiun-Tsai Lin, Taipei (TW)

(73) Assignee: Energenesis Biomedical Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,420

(22) Filed: Nov. 27, 2019

(65) Prior Publication Data

US 2020/0093829 A1 Mar. 26, 2020

Related U.S. Application Data

(63) Continuation of application No. 15/456,815, filed on Mar. 13, 2017, now Pat. No. 10,500,206.

(51) Int. Cl.
*A61K 31/52* (2006.01)
*A61K 45/06* (2006.01)
*A61K 9/00* (2006.01)

(52) U.S. Cl.
CPC ............ *A61K 31/52* (2013.01); *A61K 9/0014* (2013.01); *A61K 45/06* (2013.01)

(58) Field of Classification Search
CPC ....... A61K 31/52; A61K 9/0014; A61K 45/06
See application file for complete search history.

(56) References Cited

U.S. PATENT DOCUMENTS

| | | | |
|---|---|---|---|
| 5,547,942 A | 8/1996 | Rapaport | |
| 5,840,705 A | 11/1998 | Tsukada et al. | |
| 6,312,663 B1 | 11/2001 | Boykin, Jr. | |
| 6,342,484 B1 | 1/2002 | Kulkarni et al. | |
| 6,379,666 B1 | 4/2002 | Tobinick | |
| 10,335,412 B2 | 7/2019 | Chen et al. | |
| 10,500,206 B2 | 12/2019 | Chen et al. | |
| 2007/0021342 A1 | 1/2007 | Breen et al. | |
| 2007/0254853 A1 | 11/2007 | Van Buren et al. | |
| 2008/0228456 A1 | 9/2008 | Clermont et al. | |
| 2009/0131537 A1* | 5/2009 | Wille, Jr. ............... | A61K 45/06 514/725 |
| 2010/0009927 A1 | 1/2010 | Alberte et al. | |
| 2011/0213020 A1 | 9/2011 | Escaich Ferrer et al. | |
| 2011/0288106 A1 | 11/2011 | MUeller et al. | |
| 2019/0269688 A1 | 9/2019 | Chen et al. | |
| 2019/0269689 A1 | 9/2019 | Chen et al. | |
| 2019/0269690 A1 | 9/2019 | Chen et al. | |

FOREIGN PATENT DOCUMENTS

| | | |
|---|---|---|
| CN | 105879006 A | 8/2016 |
| EP | 2342978 A2 | 7/2011 |
| WO | 1995/01097 A1 | 1/1995 |
| WO | WO 9937151 * | 1/1999 |

OTHER PUBLICATIONS

Kedar, Can we prevent Parkinson's and Alzheimer's disease? J Postgrad Med. Jul.-Sep. 2003;49(3):236-45.
Skoog et al., Cytokinins: Structure/Activity Relationships. Phytochemistry. 1967;6:1169-92.
Vingtdeux et al., Novel synthetic small-molecule activators of AMPK as enhancers of autophagy and amyloid-beta peptide degradation. FASEB J. Jan. 2011;25(1):219-31.
Wroblewska, The Influence of Adenine and Benzyladenine on Rooting and Development of Fuchsia hybrida Cuttings. Acta Agrobotanica. 2012;65(4):101-8.
Young et al., Investigation of the effects and molecular mechanism of adenine for diabetic wound healing. EASD Virtual Meeting, 1 page, ePoster #970, Sep. 13, 2016.
U.S. Appl. No. 13/859,741, filed Apr. 10, 2013, U.S. Pat. No. 10,335,412, Issued.
U.S. Appl. No. 16/419,884, filed May 22, 2019, 2019-0269688, Published.
U.S. Appl. No. 16/419,892, filed May 22, 2019, 2019-0269689, Published.
U.S. Appl. No. 16/419,927, filed May 22, 2019, 2019-0269690, Published.
U.S. Appl. No. 15/456,815, filed Mar. 13, 2017, U.S. Pat. No. 10,500,206, Issued.

* cited by examiner

*Primary Examiner* — Sahar Javanmard
(74) *Attorney, Agent, or Firm* — McCarter & English, LLP; Yu Lu

(57) ABSTRACT

Provided is a composition for wound healing, which includes adenine and a pharmaceutically acceptable salt thereof. Also provided is a method for enhancing wound healing in a subject in need thereof including administering to the subject the composition.

15 Claims, 3 Drawing Sheets

METHOD FOR ENHANCING WOUND HEALING BY ADMINISTRATING ADENINE

REFERENCE TO RELATED APPLICATION

This Application is a Continuation of U.S. patent application Ser. No. 15/456,815, filed on Mar. 13, 2017, the entire contents of which are incorporated herein by reference in their entirety.

BACKGROUND OF THE INVENTION

1. Technical Field

The present disclosure relates to a method for enhancing wound healing, especially to a method for enhancing chronic wound healing, comprising administering to a subject a composition comprising adenine and/or a pharmaceutically acceptable salt thereof in an effective amount to enhance healing of the wound.

2. Description of Related Art

Wound healing is a dynamic tissue remodeling process involving the formation of a matrix rich in fibrin and fibronectin in the wound field, infiltration of neutrophils and macrophages, proliferation of epidermal keratinocytes at the wound edges and their migration through the provisional matrix, formation of granulation tissue containing newly developed vessels and migrating inflammatory cells and fibroblasts, and wound contraction. An ideally healed wound is one that restores normal anatomical structure, function, and appearance on cellular, tissue, organ, and organism levels. In general, with proper treatment, it will take one to two weeks for a wound to heal.

Wounds that do not heal at normal or expected rates, including chronic wounds, such as diabetic foot ulcers (major complications of diabetes resulting in lower-limb amputations), pressure ulcers, and venous ulcers, are an increasing worldwide problem and severely compromise the quality of life for large numbers of people or even result in death. Chronic wounds, which are often considered as wounds that do not heal within three months, seem to be detained in one or more of the phases of wound healing. For example, chronic wounds often remain in the inflammatory stage for too long.

Despite advances in the understanding of the principles underlying the wound healing process, there remains a significant unmet need for suitable therapeutic options for wound care and tissue repair, particularly delayed-healing wounds such as chronic ulcers and burns. Accordingly, there is a need in the art for improved methods and compositions for increasing wound healing processes.

It has been reported that adenosine 5'-monophosphate-activated protein kinase (AMPK) modulating energy metabolism may potentially target the strong association between cellular energy supply and various disease such as diabetes, cancer and cardiovascular disease. Herein, we identified that adenine as AMPK activator has a novel activity of enhancing wound healing process, and completed the present disclosure.

SUMMARY OF THE INVENTION

In view of the foregoing, the present disclosure provides a composition for wound healing, comprising adenine and a pharmaceutically acceptable salt thereof. The composition for wound healing of the present disclosure can efficiently enhance the process of wound healing.

The present disclosure further provides a method for enhancing healing of a wound in a subject in need thereof, comprising administering to the subject a composition comprising adenine and/or a pharmaceutically acceptable salt thereof in an effective amount to enhance the healing of the wound in the subject.

According to one embodiment of the present disclosure, the wound may appear in at least one tissue of the subject selected from the group consisting of skin, mouth tissue, gingiva, and corneal epithelium.

According to one embodiment of the present disclosure, the wound may be a chronic wound, including a diabetic ulcer, a venous ulcer, a pressure ulcer, a vasculitic ulcer, a mouth ulcer, an arterial ulcer, a sickle cell ulcer, a corticosteroid-induced wound, and a burn.

According to one embodiment of the present disclosure, the composition can active AMPK and/or lower inflammation in the subject as well as promote at least one of re-epithelialization and matrix deposition of the wound. In an embodiment, the composition also suppresses fibroblast proliferation and thereby prevents scar formation during the wound healing.

According to one embodiment of the present disclosure, the adenine and/or the pharmaceutically acceptable salt thereof in the composition is in an amount of between 0.0001% and 5% by weight. In an embodiment, a lower limit of the amount is 0.0002%, 0.0005%, 0.001%, 0.002%, 0.005%, 0.008%, 0.01% or 0.015%, and an upper limit of the amount is 4.8%, 4.5%, 4%, 3.5%, 3%, 2.5%, 2%, 1.8%, 1.5%, 1.2%, 1%, 0.8%, 0.5%, 0.2%, 0.15%, 0.1%, 0.08%, 0.05% or 0.02%.

According to one embodiment of the present disclosure, the adenine or the pharmaceutically acceptable salt thereof serves as an active ingredient for wound healing in the composition. In another embodiment, the adenine or the pharmaceutically acceptable salt thereof may serve as the only active ingredient for wound healing in the composition. In yet another embodiment, the adenine or the pharmaceutically acceptable salt thereof may serve in combination with an additional drug for wound healing.

Thus, the present disclosure relates to adenine and a pharmaceutically acceptable salt thereof and their use in the improvement of wound healing.

DETAILED DESCRIPTION OF THE INVENTION

Figure 1:
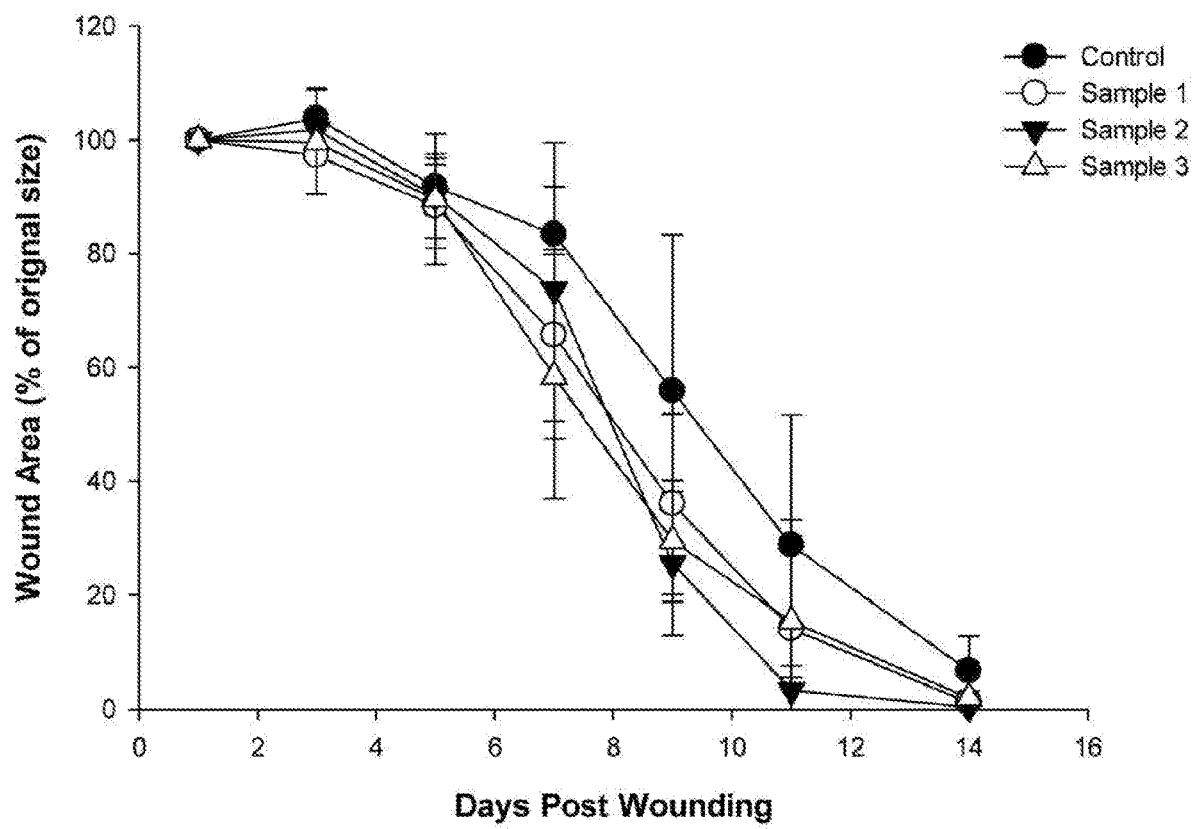
FIG. 1 shows a curve graph of wound areas coated with the compositions in a solution form comprising different concentrations of adenine of an embodiment of the present disclosure.

The following specific examples are used to exemplify the present disclosure. A person of ordinary skills in the art can conceive the other advantages of the present disclosure, based on the disclosure of the specification of the present disclosure. The present disclosure can also be implemented or applied as described in different specific examples. It is possible to modify and or alter the above examples for carrying out this disclosure without contravening its spirit and scope, for different aspects and applications.

To be noted, as used in the specification, unless clearly define an indicated object, otherwise the singular formats of "a" and "the" include plural indicated objects. Unless indicated in the context of the specification, otherwise the terminology of "or" is interchangeable with the terminology of "and/or."

In order to solve the issues in prior art, the inventors provide a composition containing adenine and/or a pharmaceutically acceptable salt thereof.

According to another aspect of the present disclosure, the inventors provide a method for enhancing healing of a wound in a subject in need thereof. In one embodiment of the present disclosure, the subject may be a mammal subject, such as human and mouse. In one embodiment, the mammal is a human mammal In one embodiment, the mammal is a non-human mammal.

In an embodiment of the present disclosure, the method comprises administering the aforesaid composition to the subject to enhance the healing of the wound in the subject.

In an embodiment of the present disclosure, the adenine and/or the pharmaceutically acceptable salt thereof as an active ingredient presented in the composition may be in an amount of between 0.0001% and 5%. In one embodiment of the present disclosure, the adenine and/or the pharmaceutically acceptable salt thereof in the composition may be in an amount of between 0.0001% and 2%. In one embodiment of the present disclosure, the adenine and/or the pharmaceutically acceptable salt thereof in the composition may be in an amount of between 0.0001% and 1%. In one embodiment of the present disclosure, the adenine and/or the pharmaceutically acceptable salt thereof in the composition may be in an amount of between 0.001% and 1%. In one embodiment of the present disclosure, the adenine and/or the pharmaceutically acceptable salt thereof in the composition may be in an amount of between 0.005% and 0.08%. In one embodiment of the present disclosure, the adenine and/or the pharmaceutically acceptable salt thereof in the composition may be in an amount of between 0.005% and 0.02%.

In an embodiment of the present disclosure, the wound may appear in at least one tissue of the subject selected from the group consisting of skin, mouth tissue, gingiva, and corneal epithelium. In one embodiment of the present disclosure, the wound may be a chronic wound.

As used herein, the term "chronic wound" refers generally to a wound that has not healed within about three months, but can be wounds that have not healed within about one or two months. Chronic skin wounds include, for example, a diabetic ulcer, a venous ulcer, a pressure ulcer, a vasculitic ulcer, mouth ulcers, an arterial ulcer, sickle cell ulcers, corticosteroid-induced wounds, burns and mixed ulcers. The chronic wound may be an arterial ulcer that can include ulcerations resulting from complete or partial arterial blockage. The chronic wound may be a venous stasis ulcer, which is associated with long-standing venous hypertension of the lower extremity resulting from a malfunction of the venous valve and the related vascular disease. The chronic wound may be a trauma-induced ulcer.

In one embodiment of the present disclosure, the chronic wound may be a diabetic foot ulcer. Diabetic patients with exemplary diabetic foot ulcer are prone to foot ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy can lose the ability to sense a sustained pressure insult and, as a result, tissue ischemia and necrosis may occur leading to, for example, plantar ulcerations. Additionally, microfractures in the bones of the foot, if unnoticed and untreated, may result in disfigurement, chronic swelling, and additional bony prominences. Microvascular disease is one of the significant complications for diabetics that may also lead to ulcerations.

In one embodiment of the present disclosure, the chronic wound may be a pressure ulcer, also known as pressure sore, bedsore and decubitus ulcer, which are localized injuries to the skin and/or underlying tissue that usually occur over a bony prominence as a result of pressure, or pressure in combination with shear and/or friction.

In one embodiment of the present disclosure, the chronic wound may be a burn including, for example, wounds that occur as a result of a burn injury, including a first degree burn (i.e., superficial, reddened area of skin); a second degree burn (a blistered injury site which may heal spontaneously after the blister fluid has been removed); a third degree burn (burn through the entire skin and usually require surgical intervention for wound healing); scalding (may occur from scalding hot water, grease or radiator fluid); a thermal burn (may occur from flames, usually deep burns); a chemical burn (may come from acid and alkali, usually deep burns); an electrical burn (either low voltage around a house or high voltage at work); an explosion flash (usually superficial injuries); and contact burns (usually deep and may occur from muffler tail pipes, hot irons, and stoves).

In an embodiment of the present disclosure, the wound may be caused by diabetes, pressure or scald burns.

In an embodiment of the present disclosure, the adenine and/or the pharmaceutically acceptable salt thereof presented in the composition is useful for activating AMPK.

As used herein, the term "AMPK" is a cellular energy sensor and a responder to energy demand. AMPK is a heterotrimer composed of catalytic subunit and regulatory $\beta$, $\gamma$ subunits. All these subunits are highly conserved in eukaryotes. The activation of AMPK is through phosphorylation on the conserved $172^{th}$-threonine residue of $\alpha$ subunit by upstream kinases such as LKB1, $Ca^{2+}$/Calmodulin dependent kinase, and TAK1. High AMP/ATP ratio caused by physiological or pathological stress activates AMPK. Upon activation, AMPK activates catabolic pathway and inhibits anabolism which in term restores cellular energy balance by decreasing ATP consumption and promoting ATP generation.

In one embodiment of the present disclosure, the composition containing adenine and/or the pharmaceutically acceptable salt thereof can active AMPK in the subject. In another embodiment of the present disclosure, the composition can also lower inflammation in the subject as well as promote at least one of re-epithelialization and matrix deposition of the wound, thereby effectively improving and enhancing the process of wound healing. In yet another embodiment, the composition can suppress fibroblast proliferation and thereby prevent scar formation during the wound healing.

In an embodiment of the present disclosure, the composition may be administered once daily for 7 days to 30 days. In another embodiment of the present disclosure, the composition may be administered once daily for 14 days to 28 days.

In an embodiment of the present disclosure, the composition may be administered to the subject through topical administration or systemic administration.

In one embodiment of the present disclosure, the composition may be formulated in one form selected from the group consisting of a solution, a liniment, a lotion, a spray, an aerosol, an ointment, a foam, a cream, a gel, a paste, a patch, a glue, a film, an orabase, a powder, and a wound dressing.

The following are specific embodiments further demonstrating the efficacy of the current disclosure, but not to limit the scope of the current disclosure.

EXAMPLES

Preparation Example 1

Preparation of Compositions Containing Different Concentrations of Adenine in a Form of Solution The method for preparing compositions containing different concentrations of adenine in a solution form was shown as follows. Different quantities of adenine were respectively dissolved in 0.9% sodium chloride solution at room temperature, allowing the solutions respectively to contain 0.005%, 0.02%, and 0.08% adenine, so as to obtain colorless solutions respectively named as Samples 1, 2 and 3. On the other hand, a composition without adenine was used as Control.

Preparation Example 2

Preparation of Composition Containing 0.02% of Adenine in a Form of Gel

The method for preparing composition containing 0.02% of adenine in a gel form was shown as follows. 6.2 g sodium chloride, 1.6 g methylparaben, 0.2 g propylparaben and 0.2 g adenine were dissolved in 1000 ml distilled water, followed by adding 30 g carboxylmethylcellulose at room temperature, so as to obtain a colorless gel containing 0.02% adenine and named as Sample 4. On the other hand, a composition without adenine was used as Control.

Preparation Example 3

Animals for Evaluating Diabetic Wound Healing with Compositions Containing Different Concentrations of Adenine in a Form of Solution The BKS. Cg-Dock7$^m$+/+Lepr$^{db}$/Jnarl (db/db) male mice approximately at 8 to 11 weeks of age were purchased from the National Laboratory Animal Center (NLAC, R.O.C.). A total of 20 males with healthy and intact skin were used for the test for diabetic wound healing. The mice were each identified by a cage tag. The db/db has been the species of choice to evaluate the efficacy for diabetic wound healing.

The mice were housed individually in a plastic cage with stainless steel wire lid, and were quarantined and acclimated for over 2 weeks prior to test for diabetic wound healing. The temperature and relative humidity were in the range stipulated in the protocol at 21±2° C. and 55±10%, respectively. A 12-h/12-h light/dark cycle was maintained with light on at 7:00 AM and off at 7:00 PM.

Preparation Example 4

Animals for Evaluating Diabetic Wound Healing with Composition Containing 0.02% of Adenine in a Form of Gel The BKS. Cg-Dock7$^m$+/+Lepr$^{db}$/Jnarl (db/db) male mice at 8 weeks of age were purchased from the National Laboratory Animal Center (NLAC, R.O.C.). A total number of 10 mice with healthy and intact skin were used for the test for diabetic wound healing. The average±SEM body weight of the mice was 34.5±1.5 g. All mice had fasting blood glucose levels over 300 mg/dL.

The mice were housed individually in stainless steel cage, and were quarantined and acclimated for at least one week prior to test for diabetic wound healing. The temperature and relative humidity were in the range stipulated in the protocol at 21±2° C. and 55±10%, respectively. A 12-h/12-h light/dark cycle was maintained with light on at 7:00 AM and off at 7:00 PM.

Example 1

Effect of Compositions Containing Different Concentrations of Adenine in a Form of Solution on Diabetic Wound Healing The method for applying the compositions containing different concentration of adenine to the diabetic wound of mice was shown as follows. The mice described in Preparation example 3 were randomly divided into four groups of five animals each and then were anesthetized with isoflurane by use of an anesthesia system for rodents (Matrx™ VIP 3000 isoflurane vaporizer, Midmark). Before wounding, the dorsal surface of each mice was shaved, and then sterilely prepped with 70% ethanol for surgery. A full thickness wound was created by a 8-mm sterile skin biopsy punch. 100 µL of each composition (Samples 1 to 3 and Control as described in Preparation example 1) was applied on the wound bed immediately after surgery and once daily for 14 days.

Wounds of each mice were photographed everyday with standardized exposure and focal lengths using a digital camera (Lumix DMC-GF1, Panasonic). All images were analyzed by use of image analysis software (Image ProPlus, Media Cybernetics, Version 6.0). Each image was analyzed to calculate the wound area (tracing the border of the wound). The wound area of each mice at each time point was calculated by the following formula:

$$\text{Wound area (\% of original wound area)} = \frac{\text{wound area of the mice on Day N}}{\text{wound area of the mice on Day 1}} \times 100.$$

The results were shown in Table 1 and FIG. 1. The results showed that the compositions containing different concentrations of adenine could efficiently enhance the process of diabetic wound healing.

TABLE 1

Individual wound area (% of original wound area)

| Composition | Animal ID | D 1 | D 3 | D 5 | D 7 | D 9 | D 11 | D 14 |
|---|---|---|---|---|---|---|---|---|
| Control | 1 | 100.0 | 103.3 | 84.9 | 91.7 | 38.6 | 12.8 | 2.2 |
|  | 2 | 100.0 | 96.1 | 89.7 | 75.5 | 25.7 | 6.5 | 0.0 |
|  | 3 | 100.0 | 112.6 | 100.6 | 86.5 | 80.0 | 38.5 | 6.9 |
|  | 4 | 100.0 | 104.7 | 91.5 | 71.2 | 38.6 | 16.0 | 7.1 |
|  | 5 | 100.0 | 102.3 | 91.9 | 91.7 | 96.5 | 69.4 | 17.4 |
| Sample 1 (0.005% adenine) | 1 | 100.0 | 102.3 | 85.9 | 69.2 | 52.5 | 42.8 | 5.1 |
|  | 2 | 100.0 | 88.6 | 86.2 | 72.7 | 24.3 | 3.7 | 0.0 |
|  | 3 | 100.0 | 106.5 | 102.6 | 35.9 | 20.5 | 1.8 | 0.0 |
|  | 4 | 100.0 | 98.9 | 85.9 | 77.6 | 24.7 | 0.6 | 0.0 |
|  | 5 | 100.0 | 90.3 | 81.1 | 72.6 | 58.0 | 21.1 | 0.7 |
| Sample 2 (0.02% adenine) | 1 | 100.0 | 99.8 | 103.0 | 95.5 | 47.5 | 11.4 | 1.7 |
|  | 2 | 100.0 | 103.0 | 84.7 | 80.8 | 29.7 | 4.2 | 0.0 |
|  | 3 | 100.0 | 108.1 | 90.4 | 96.6 | 22.6 | 0.8 | 0.0 |
|  | 4 | 100.0 | 98.9 | 81.0 | 69.4 | 16.9 | 0.0 | 0.0 |
|  | 5 | 100.0 | 99.1 | 91.4 | 25.6 | 10.9 | 0.0 | 0.0 |
| Sample 3 (0.08% adenine) | 1 | 100.0 | 84.1 | 73.2 | 34.3 | 24.4 | 3.7 | 0.0 |
|  | 2 | 100.0 | 95.7 | 83.1 | 68.4 | 34.7 | 24.1 | 9.2 |
|  | 3 | 100.0 | 111.3 | 106.1 | 31.1 | 15.3 | 1.1 | 0.0 |
|  | 4 | 100.0 | 103.2 | 86.8 | 81.9 | 26.0 | 1.1 | 0.0 |
|  | 5 | 100.0 | 103.7 | 98.4 | 76.2 | 46.8 | 46.7 | 0.7 |

Example 2

Effect of Composition Containing 0.02% of Adenine in a Form of Gel on Diabetic Wound Healing The method for applying the composition containing 0.02% of adenine to the diabetic wound of mice was shown as follows. The mice described in Preparation example 4 were randomly divided into two groups of five animals each and then were anesthetized with isoflurane by use of an anesthesia system for rodents (Matrx™ VIP 3000 isoflurane vaporizer, Midmark). The fur of each mice was removed from the base of neck to 3 cm further down the back and between the two shoulder blades by clippers, optionally followed by applying with depilatory cream for no longer than 2 min. Wet gauze swabs could be used to ensure all cream and remaining fur was removed. After then, the shaved dorsal surface of each mice was sterilely prepped with 70% ethanol for surgery. A full thickness wound was created by a 8-mm sterile skin biopsy punch. Wounds was adhered with silicone splint and sutured to the wound perimeter to prevent wound contraction. 100 μL of each composition (Samples 4 and Control as described in Preparation example 2) was applied on the wound bed immediately after surgery and once daily for 15 days.

Wounds of each mice were photographed everyday with standardized exposure and focal lengths using a digital camera (Lumix DMC-GF1, Panasonic), and wound areas were analyzed and calculated according to the analysis as described in Example 1.

Figure 2:
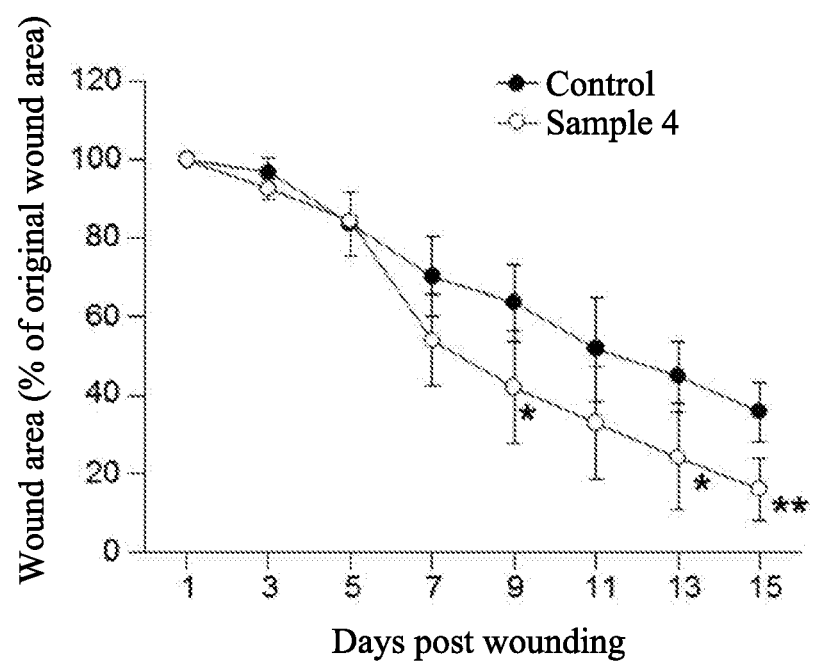
FIG. 2 shows a curve graph of wound areas coated with the compositions in a gel form comprising 0.02% of adenine of an embodiment of the present disclosure.

The results were shown in Table 2 and FIG. 2. Data shown in FIG. 2 are presented as the mean±SD (one-way ANOVA; *, $p<0.05$; **, $p<0.01$; specific comparison to Control). The results showed that the compositions containing 0.02% of adenine in a form of gel could efficiently enhance the process of diabetic wound healing.

TABLE 2

Individual wound area (% of original wound area)

| Group | Animal ID | Day 1 | Day 3 | Day 5 | Day 7 | Day 9 | Day 11 | Day 13 | Day 15 |
|---|---|---|---|---|---|---|---|---|---|
| Control | 1 | 100 | 103.2 | 92.3 | 68.3 | 57.6 | 46.8 | 36.7 | 28.4 |
|  | 2 | 100 | 97.3 | 68.5 | 53.0 | 47.6 | 31.7 | 36.5 | 28.6 |
|  | 3 | 100 | 93.1 | 84.5 | 70.7 | 67.2 | 50.3 | 39.6 | 32.3 |
|  | 4 | 100 | 97.2 | 89.5 | 83.9 | 71.5 | 57.8 | 54.1 | 45.3 |
|  | 5 | 100 | 94.1 | 84.0 | 75.5 | 74.1 | 72.5 | 57.4 | 43.7 |
| Sample 4 (0.02% adenine) | 1 | 100 | 91.9 | 85.8 | 41.3 | 26.8 | 27.1 | 16.7 | 12.5 |
|  | 2 | 100 | 96.9 | 83.0 | 43.4 | 32.2 | 28.1 | 22.8 | 20.8 |
|  | 3 | 100 | 94.2 | 85.8 | 53.3 | 41.9 | 28.2 | 15.3 | 6.0 |
|  | 4 | 100 | 90.3 | 84.4 | 58.1 | 40.5 | 20.6 | 15.5 | 12.7 |
|  | 5 | 100 | 90.1 | 83.6 | 73.9 | 68.6 | 61.0 | 51.1 | 28.9 |

Example 3

AMPK Activation Assay

Effects of adenine on AMPK activation were evaluated based on the phosphorylation of AMPK and Acetyl-CoA carboxylase (ACC) protein upon adenine treatment. The process of animal experiment was the same as Example 2, except that after 12 days post wounding, skin tissues of db/db mice were homogenized and subject to western blot analysis. Equal amount of proteins from each sample was separated by SDS-PAGE and then electroblotted on to PVDF membranes. Membranes were blocked with 3% BSA in PBS for 60 mins and incubated with an anti-phospho-AMPK (Thr172) antibody (1:2000, Cell Signaling), an anti-AMPK antibody (1:2000, Cell Signaling), an anti-ACC antibody (1:1000, Cell Signaling) or an anti-phospho-ACC antibody (1:1000, Cell Signaling) at 4° C. overnight followed by the corresponding secondary antibody for 1 h at room temperature (RT). Immunoreactive bands were detected by enhanced chemiluminescence (ECL; Pierce, Rockford, Ill., USA) and recorded using Kodak film (Rochester, N.Y., USA). The detected signals were scanned and then quantified using ImageJ software.

Figure 3:
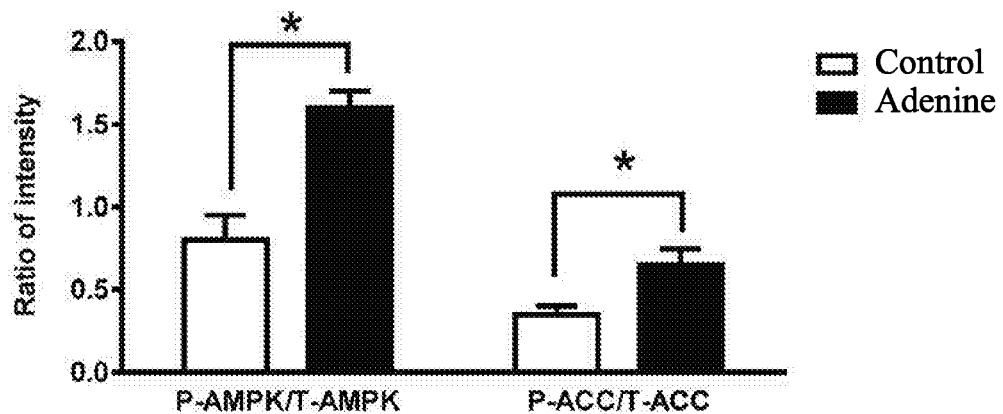
FIG. 3 shows the effect of adenine on AMPK activation in regenerated skin tissue of diabetic mice.

The results were shown in FIG. 3, indicating that the adenine could efficiently enhance phosphorylation level of AMPK and ACC in regenerated skin tissue.

Example 4

ATP Assay

The process of animal experiment was the same as Example 2, except that after 12 days post wounding, skin tissues of db/db mice were homogenized and centrifuged for 10 mins with 8,000 rpm at 4° C. Supernatant from tissue lysate was filled up in the column and spun down at 1,000×g for 2 minutes. 10 µL of eluate was analyzed using ATP colorimetric assay kit (Biovision).

Figure 4:
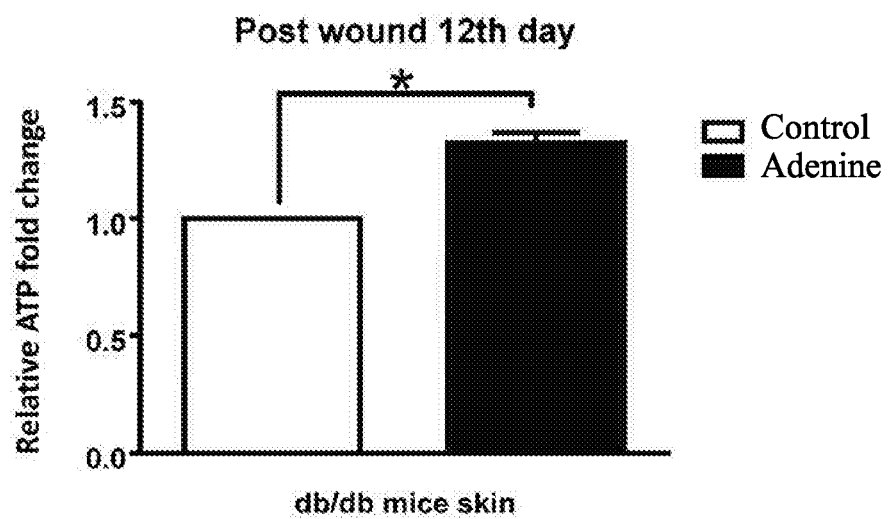
FIG. 4 shows the effect of adenine on increasing ATP in regenerated skin tissue of diabetic mice.

The results were shown in FIG. 4, indicating that the adenine could efficiently increase ATP level in regenerated skin tissue.

Example 5

Effect of Compositions Containing Adenine in an Amount of Between 1 and 4,000 µM on Scald Burns Healing The C57BL/6 mice approximately at 8 weeks of age were purchased from the National Laboratory Animal Center (NLAC, R.O.C.). The mice were deeply anesthetized by injecting intraperitoneally normal saline mixed with zoletil 50 and 2% rompun in a ratio of 2:1:1 (2 µl per gram of body weight). Each of the mice was shaved by depilatory cream. The shaved dorsal surface of each mice was sterilized with 70% ethanol and then the mice were placed in a restrainer with a 2×3 cm hole at the top. The dorsal surface of mice was exposed toward the hole of restrainer. The water at 60° C. was applied to the dorsal surface of mice for 40 seconds, followed by water at 4° C. for 45 seconds. The mice of Control group was only applied with water at 4° C. for 45 seconds. After scalding, each of the mice was then individually placed in a cage, and fed with diazepam in the drinking water (50 mg/L) for the early 7 days. The mice were monitored every day for body weight of and wound infections.

After scalding, the compositions containing 1 µM to 4,000 µM adenine in normal saline or only normal saline as Control were individually applied on the scald burn wound of mice once daily for 28 days.

Wounds of each mice were photographed everyday with standardized exposure and focal lengths using a digital camera (Lumix DMC-GF1, Panasonic), and wound areas were analyzed and calculated according to the analysis as described in Example 1.

The results showed that the compositions containing adenine in an amount of between 1 and 4,000 µM could efficiently decrease inflammatory response and enhance the process of healing of scald burns wound.

Example 6

Effect of Compositions Containing Adenine in an Amount of Between 1 and 4,000 µM on Pressure Ulcer Healing The C57BL/6 mice approximately at 8 weeks of age were purchased from the National Laboratory Animal Center (NLAC, R.O.C.). The mice were anesthetized with isoflurane using anesthesia system for rodents (Matrx™ VIP 3000 isoflurane vaporizer, Midmark). Before wounding, the dorsal surface was shaved and sterilely prepped with 70% ethanol for surgery. Dorsal skin was positioned between 2 circular magnets having 12-mm diameter for 12 hours and removed from them for 12 hours for 1 ischemia-reperfusion cycle. Pressure ulcer was created by 2 ischemia-reperfusion cycles. The force generated between the 2 magnets was 0.183N for a 5-mm skin bridge between the 2 magnets.

After 2 ischemia-reperfusion cycles, the compositions containing 1 µM to 4,000 µM adenine in normal saline or only normal saline as Control were individually applied on the pressure ulcer wound of mice once daily for 14 days.

Wounds of each mice were photographed everyday with standardized exposure and focal lengths using a digital camera (Lumix DMC-GF1, Panasonic), and wound areas were analyzed and calculated according to the analysis as described in Example 1.

The results showed that after 14 day of treatment, the extent of closure was significantly greater in adenine treated mice in dose-dependent manner than in control mice. Thus, the compositions containing adenine in an amount of between 1 and 4,000 µM could efficiently enhance the process of healing of pressure ulcer wound.

Example 7

Adenine Inhibited Fibroblast Proliferation

Human fibro blast cell line 3T3 were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibeoBRL, Carlsbad, Calif., USA) at 37° C. under 5% $CO_2$. For cell proliferation assay, 3T3 cells were plated at $1 \times 10^5$ per well (6-well plate). 24 h after plating, cells were treated with indicated concentration of adenine for 72 h and the number of viable cells was counted. Cells were detached using trypsin-EDTA solution and stained with trypan blue. The living cells were counted using hemocytometer. The effects of adenine on 3T3 cell proliferation were summarized in Table 3. Adenine significantly inhibited 3T3 cell proliferation in dose-dependent manner. Data were presented as the mean±SEM of three independent experiments.

TABLE 3

| Adenine (microM) | Cell number (% to control) |
| --- | --- |
| 0 | 100 ± 4.3 |
| 10 | 91 ± 2.7 |
| 50 | 73 ± 8.1 |
| 100 | 64 ± 5.3 |
| 200 | 48 ± 2.8 |
| 500 | 33 ± 6.4 |
| 1000 | 27 ± 11.3 |

Example 8

Adenine Enhances Wound Healing and Reduces Scar Formation

C57BL/6J mice were maintained at 22° C. under a 12-h light/dark cycle. The experiments were performed with 12-weeks old mice. After anesthetized by an intraperitoneal injection of ketamine (500 mg/kg) and xylazine (100 mg/kg), 6-mm full-thickness excisional skin wounds was made on the backs of mice using 6-mm skin biopsy punches. Immediately after wounding, 1 µM to 4000 µM of adenine in 25 ml saline or saline alone was applied to the wound bed. The skin wounds were then covered by semipermeable transparent dressing and fixed to the skin. The mice were treated with adenine or vehicle for 14 days and then sacrificed. The scar formation was assessed by Masson's trichrome staining to observe the fibrosis process and the collagen framework of the healed wound (Fixed by 4% paraformaldehyde). After 14 days of treatment, the extent of closure was significantly greater in adenine treated mice in dose-dependent manner than in control mice. According to histological examination of the regenerated tissue, topical treatment with adenine significantly decreased the scar width 14 days post-wounding compared to vehicle treated wounds.

The rate of healing wounds such as chronic wounds including diabetic ulcers, pressure ulcers, and a burn may be enhanced by adenine and/or the pharmaceutically acceptable salt. The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A method for enhancing healing of a wound in a subject in need thereof, comprising administering to the subject a composition comprising adenine and/or a pharmaceutically acceptable salt thereof, in an effective amount to enhance the healing of the wound in the subject, wherein the adenine and/or the pharmaceutically acceptable salt thereof in the composition is in an amount of between 0.0001% and 0.05% by weight.

2. The method of claim 1, wherein the wound appears in at least one tissue of the subject selected from the group consisting of skin, mouth, gingiva, and corneal epithelium.

3. The method of claim 1, wherein the wound is a chronic wound.

4. The method of claim 3, wherein the chronic wound is selected from the group consisting of a diabetic ulcer, a venous ulcer, a pressure ulcer, a vasculitic ulcer, a mouth ulcer, an arterial ulcer, a sickle cell ulcer, a corticosteroid-induced wound, a burn and a combination thereof.

5. The method of claim 4, wherein the diabetic ulcer is a diabetic foot ulcer.

6. The method of claim 1, wherein the composition activates adenosine 5'-monophosphate-activated protein kinase (AMPK) in the subject.

7. The method of claim 1, wherein the composition lowers inflammation in the subject.

8. The method of claim 1, wherein the composition suppresses fibroblast proliferation and prevents scar formation during the healing of the wound.

9. The method of claim 1, wherein the adenine and/or the pharmaceutically acceptable salt thereof in the composition is in an amount of between 0.001% and 0.05% by weight.

10. The method of claim 9, wherein the adenine and/or the pharmaceutically acceptable salt thereof in the composition is in an amount of between 0.005% and 0.05% by weight.

11. The method of claim 10, wherein the adenine and/or the pharmaceutically acceptable salt thereof in the composition is in an amount of between 0.01% and 0.05% by weight.

12. The method of claim 1, wherein the adenine and/or the pharmaceutically acceptable salt thereof is administered to the subject through topical administration or systemic administration.

13. The method of claim 1, wherein the composition is formulated in one form selected from the group consisting of a solution, a liniment, a lotion, a spray, an aerosol, an ointment, a foam, a cream, a gel, a paste, a patch, a glue, a film, an orabase, a powder, and a wound dressing.

14. The method of claim 1, wherein the adenine and/or the pharmaceutically acceptable salt thereof serves as the only active ingredient for the healing of the wound in the composition.

15. The method of claim 1, wherein the adenine and/or the pharmaceutically acceptable salt thereof serves as in combination with an additional drug for wound healing.

* * * * *